United States Patent
Lapszynski et al.

(10) Patent No.: US 9,259,784 B2
(45) Date of Patent: Feb. 16, 2016

(54) MULTI-PART AXIAL POWDER COMPRESSION MOLD FOR COMPLEX PARTS

(71) Applicant: Howmedica Osteonics Corp., Mahwah, NJ (US)

(72) Inventors: John Lapszynski, Oak Ridge, NJ (US); Lionel Fuentes, Jr., Washington Township, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 519 days.

(21) Appl. No.: 13/786,892

(22) Filed: Mar. 6, 2013

(65) Prior Publication Data

US 2014/0255241 A1    Sep. 11, 2014

(51) Int. Cl.
  *B22F 5/10*  (2006.01)
  *B22F 3/03*  (2006.01)
  *B30B 11/04* (2006.01)
  *A61F 2/30*  (2006.01)
  *A61F 2/34*  (2006.01)

(52) U.S. Cl.
  CPC ............. *B22F 5/10* (2013.01); *A61F 2/3094* (2013.01); *B22F 3/03* (2013.01); *B30B 11/04* (2013.01); *A61F 2/34* (2013.01); *A61F 2002/30957* (2013.01); *A61F 2002/30968* (2013.01)

(58) Field of Classification Search
  CPC ........................................................ B22F 5/10
  USPC ........................................................ 419/66
  See application file for complete search history.

(56) References Cited

U.S. PATENT DOCUMENTS

| 2,894,837 A * | 7/1959 | Onstott .............. B22F 3/22 419/14 |
| 3,492,120 A * | 1/1970 | Haller ............... B22F 5/10 29/898.069 |
| 5,030,402 A | 7/1991 | Zachariades |
| 2010/0076569 A1* | 3/2010 | Langhorn .......... A61F 2/30767 623/22.21 |
| 2010/0137997 A1* | 6/2010 | Casari ............... A61L 27/56 623/23.43 |
| 2012/0213911 A1* | 8/2012 | Bucciotti ........... A61F 2/30767 427/2.26 |

OTHER PUBLICATIONS

Johnson, International Journal of Powder Metallurgy, 2011 PM Design Excellence Awards Winners, 47/4, pp. 11-16, Jul.-Aug. 2011.

* cited by examiner

*Primary Examiner* — Jessee Roe
*Assistant Examiner* — Christopher Kessler
(74) *Attorney, Agent, or Firm* — Lerner, David, Littenberg, Krumholz & Mentlik, LLP

(57) ABSTRACT

A method for manufacturing a titanium acetabular cup shell includes obtaining a titanium powder. A three part mold having a first part with a part-spherical inner surface, a second ram part with a part-spherical outer impact surface and a third ram part with an annular impact surface are provided to compact the titanium powder. The second and third parts are aligned along an axis within the first part. The second part is aligned along a center axis within the annular impact surface of the third part. The first mold part is filled with the titanium powder. The second mold part-spherical outer surface and the third part annular impact surface are moved towards the part-spherical inner surface of the first part into contact with the powder. The powder is compacted with the second part part-spherical outer impact surface and the third part annular impact surface to about 50% of its initial volume.

21 Claims, 4 Drawing Sheets

MULTI-PART AXIAL POWDER COMPRESSION MOLD FOR COMPLEX PARTS

BACKGROUND OF THE INVENTION

This invention relates to a molding method for forming part-spherical acetabular cup shell or knee femoral components from powdered metal, preferably powdered Titanium (Ti).

Parts having simple geometries, such as flat plates, can easily be compression molded. Presently molding complex geometries from metal or polymer powder is typically done using either injection molding or isostatic pressing and usually not compression molding.

Injection molding can make complicated shapes with a well-designed mold, but the molds and molding equipment can be expensive. In addition, powder additives are used to allow the powder to more easily flow in the mold. These additives can interfere with obtaining a fully dense part and be difficult to remove from the part after molding. The powder feedstock also needs to be carefully selected for its flow characteristics and can be relatively expensive. Furthermore, injection molding is performed at lower pressures which cannot deform the metal powder and therefore requires a binding agent to compact a part that can be subsequently handled/post processed. Having a binder as well as a flow enhancing agent takes up space, (often up to about 20% of the compacted part mixture) and results in a large amount of dimensional change during the sintering consolidation.

Isostatic pressing typically involves a pressure-filled bladder pressing the powder against a rigid surface. Thus, tooling and equipment costs can be less than with injection molding, but additives (such as binders) are generally still necessary. A drawback to isostatic pressing is that the quality of the surface adjacent to the bladder is not as good as can be obtained with injection molding.

Compression molding one-dimensional objects, such as a hockey puck, from powder is simple because the resulting object is the same thickness in the direction of travel of the moveable ram of the compression mold. Flat multi-level parts such as gears are more difficult to mold and normally to achieve a relatively uniform density throughout, the part multi stage tooling and/or additional pressing rams need to be used. Molding a two-dimensional object, such as a hemispherical shell, from metal powder is more difficult because even if the wall thickness of the resulting object is uniform, the thickness measured in the direction of mold or ram travel or direction of compaction can vary. Thus for an acetabular shell the radial thickness between an inner and outer part-spherical surface can be constant but varies in a direction perpendicular to the equator.

What is needed is an economical method to mold two-dimensional shapes (such as a hemisphere) from powder. In order to be economical the method should be able to utilize inexpensive powder feedstock, require no binding agent to be mixed into the powder, require no additive to improve flow characteristics of the powder, require tooling and equipment that is relatively inexpensive compared to injection molding, and allows for better surface quality on all sides of the resulting part than is possible with isostatic pressing. In some cases a die wall lubricant is used to improve the life of the mold/tool and to improve the ejection of the part out of the tool. However, it is important to keep residuals out of the part when compacting Titanium due to its high reactivity during sintering. Compression molding can achieve these objectives. In the past, the problem has been that molding parts of different thicknesses, such as an acetabular cup shell, requires different amounts of compression in the direction of compression motion in different areas of the mold. This is difficult to achieve using a mold having only one moveable compression part.

BRIEF SUMMARY OF THE INVENTION

One aspect of the invention is to provide a three-part mold having first and second moveable ram elements. The moveable ram elements allow the compaction of titanium sponge powder to form a hollow hemispherical construct suitable for use as a shell of an acetabular cup. The mold parts are located or nested within one another. Of the three mold parts, the first may be stationary with the second part nested within the third part and the third part nested within the second part. Both the moveable second and third parts are independently moveable with respect to the first mobile part. Preferably the inner second mold part has a part-spherical impact surface which forms the polar area of the part-spherical acetabular cup shell and the third part has an annular contact surface formed by two concentric cylinders forming an inner and outer wall of the third mold part. The annular contact surface compacts the powder to form the equatorial region of the part-spherical acetabular shell.

This and other aspects of the invention are achieved by a method for manufacturing a titanium acetabular cup shell accomplished by obtaining a titanium sponge powder. A three part mold is provided having a first mold part with a part-spherical inner surface, a second mold part comprising a first ram with a part-spherical outer impact surface and a third mold part comprising a second ram with an annular impact surface. The second and third parts are aligned along an axis within the first part and the second part is aligned along the axis within the third part. The second mold part is surrounded by the annular impact surface of the mold part. The axis is the central axis of both the annular impact surface and the spherical surface of the first and second parts. This axis is the polar axis which is perpendicular to the plane of the opening of the spherical bearing surface of the shell through the central point at the center of the sphere. Typically the plane of the opening of the shell spherical inner bearing surface defines the equatorial plane of the shell. The second and third mold parts move in the direction of the central axis during the impaction process. The first part which is filled with the titanium sponge powder and the second mold part-spherical outer surface and the third part annular surface move towards the part-spherical inner surface of the first part into contact with the powder either sequentially or simultaneously. The powder is compacted with the second part part-spherical outer impact surface and the third mold part annular impact surface, wherein the second and third mold parts preferably contact the powder in sequence with the second mold part contacting first. The third mold part moves at a greater velocity relative to the first mold part than the second mold part. The second mold part preferably contacts the powder prior to the third mold part contacting the powder and the second mold part remains in contact with the powder until after the third mold part contacts the now partially compacted powder. The powder is preferably compacted to about 50% of its original volume by the mold parts. Typically the third mold part moves three times as far relative to the first mold part after initially contacting the powder compared to the second mold part. The second and third mold parts impact the powder to produce a pressure of 30 to 50 tons per square inch.

Other aspects of the present invention are achieved by a process for manufacturing a titanium acetabular cup outer shell which includes providing titanium sponge powder having an average particle size less than 20 mesh. A mold having three parts aligned along an axis is provided. The three part mold has a first mold part comprising a part-spherical inner surface, a second mold part comprising a part-spherical outer impact surface and a third mold part having an annular impact surface. The second part and third part are preferably moveable with respect to the first mold part part-spherical inner surface. The movement is along an axis forming a central axis of the part-spherical first and second mold part spherical surfaces and the third mold part impact surface is an annular surface formed by concentric inner and outer cylindrical wall surfaces. The diameter of the inner cylindrical surface of the third mold part is greater than a maximum diameter of the part-spherical outer surface of the second part and the outer cylindrical diameter of the third mold part less than a maximum diameter of the part-spherical inner surface of the first part. Thus, the second part is nested within the third mold part and the third part is nested in the first part. The first mold part with the Ti sponge powder placed therein is compacted with the second and third parts to form a part-spherical compact which is sintered to form the shell.

The powder filling a mold needs to be compressed about 50 percent of its original volume to make a fully dense part, then sintered to make the part as shown in FIG. 1. The compression mold second part needs to move one unit (two units of powder thickness pressed down to one unit of dense material) shown as B in FIG. 1. However, at the side (towards the equator) the third mold part needs to move three units (six units of powder thickness pressed down to three units of thickness) shown as "A" in FIG. 1.

The commercially pure Titanium sponge powder used has over 98 percent Titanium by weight and is sieved to 20 mesh average particle size. Such material may be obtained from Global Titanium Inc. of Detroit, Mich. 48234. FIGS. 2-4 show a three-part compression mold with two moveable ram ports being used in a sequential operation. However, more than two moveable rams could also be employed. In addition, the motions of the two (or more) rams could occur simultaneously rather than sequentially. If the two rams or mold parts are moving simultaneously over the same period of time but one ram has a longer travel distance then that ram will need to move at a greater average velocity.

This type of mold is particularly useful to forming orthopedic implants such as acetabular shells and femoral components for total knee replacements. A material appropriate for making implants using the two-part compression mold is "sponge titanium" conforming to ASTM 1580. Sponge Titanium is available for approximately $17-20 per pound but is not well suited for use in injection molds. Other powder forms of Ti are HDH irregular shape (which also can conform to ASTM 1580 but costs $85-$100 per pound), and spherical Ti powder with good flow characteristics ($150-$400 per pound). In general that spherical powder will comprise about 50 percent of the cost of most parts made with the powder. The high cost of this specialized new material can make it difficult to be competitive for many parts. See http://ammtiac.alionscience.com/pdf/AMPQ6_2ART01.pdf, for one of many articles around the topic of high cost titanium.

In addition, sponge titanium can be elementally blended with other metal powder to create alloy such as Ti-6Al-4V. A suitable pressure for compressing any titanium or titanium alloy powder is one that gets as close to 100 percent density as possible without overworking the metal and creating frangible object. It has been found that when using this type of mold with sponge titanium to make, for example an acetabular cup hemisphere a pressure of 30-50 tons per square inch (Tsi) is suitable.

While the acetabular cup may have a uniform thickness, its thickness along an axis through a center of the sphere and a pole of the sphere varies from the pole to the equator. In other words, the amount of powder that has to be compacted in the equator area is up to three times greater than the amount of powder that has to be compacted in the polar area

DETAILED DESCRIPTION

Figure 1:
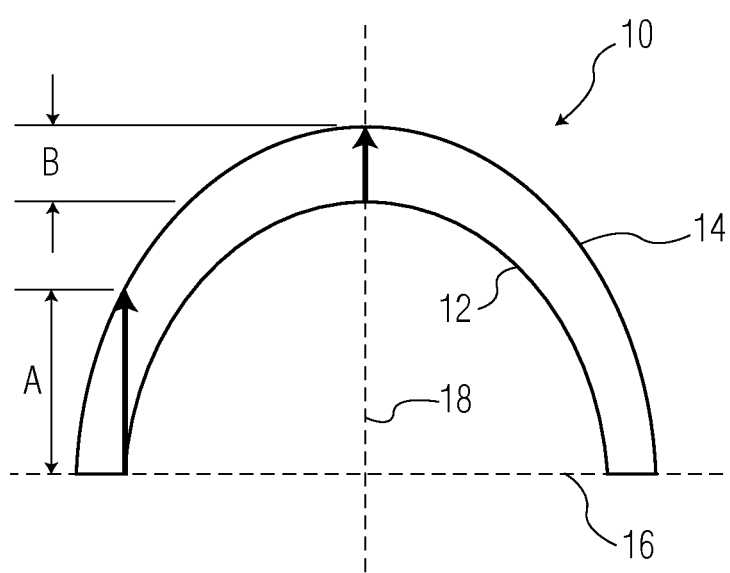
Referring to FIG. 1 there is shown a cross-section of a typical acetabular cup shell having a generally hemispherical or part-spherical shape which shell is to be implanted in a prepared acetabulum.

Referring to FIG. 1 there is shown a cross-section of the acetabular cup with a part-spherical hemispherical shape of any well-known design. The cup is made of sintered fully dense compacted titanium powder. The cup generally denoted as 10 includes an inner spherical surface 12 and an outer spherical surface 14 defining a wall therebetween which may be thicker at the pole than at the equator. Surface 12 of cup 10 has an equatorial region lying along plane 16 and a polar region lying along axis 18.

Figure 2:
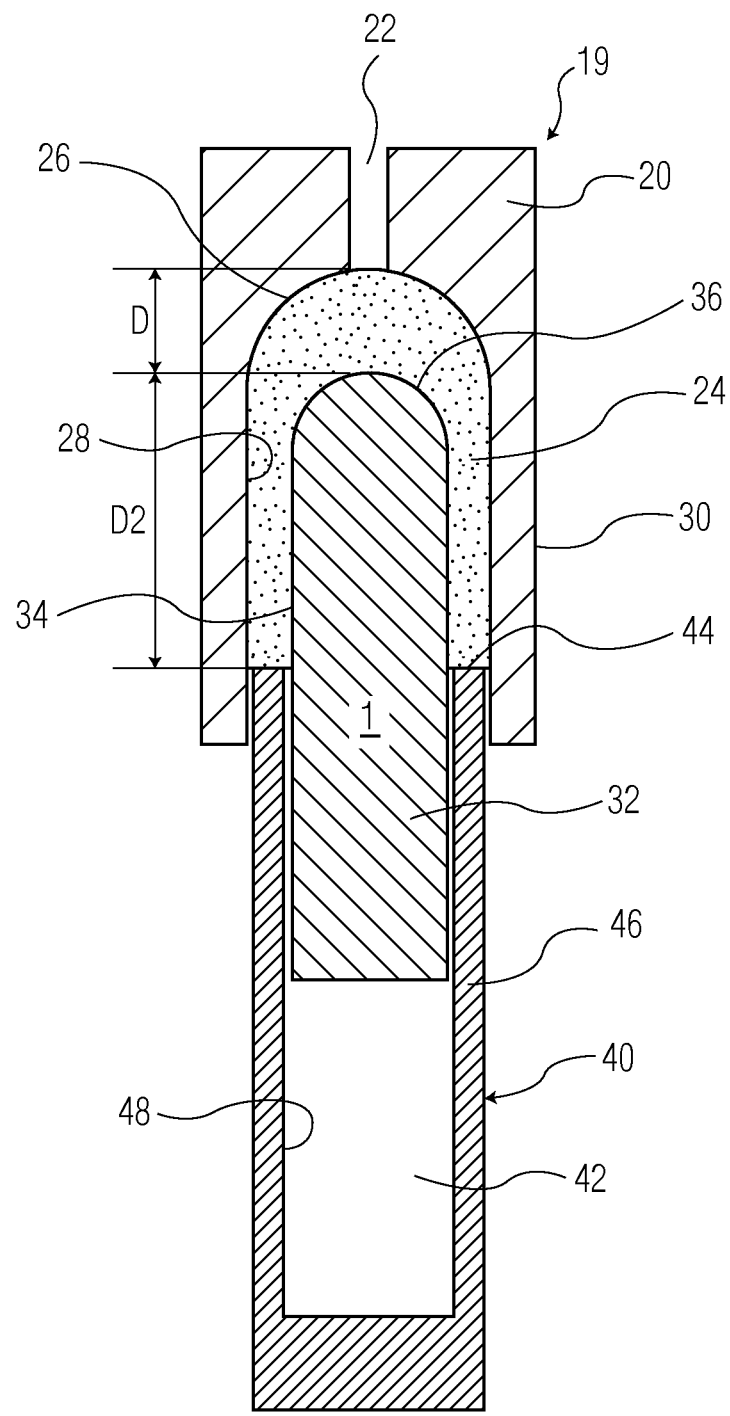
FIG. 2 shows a cross-sectional three part view of the mold used to compact the cup of FIG. 1 in a starting position prior to being filled with powder.
Figure 3:
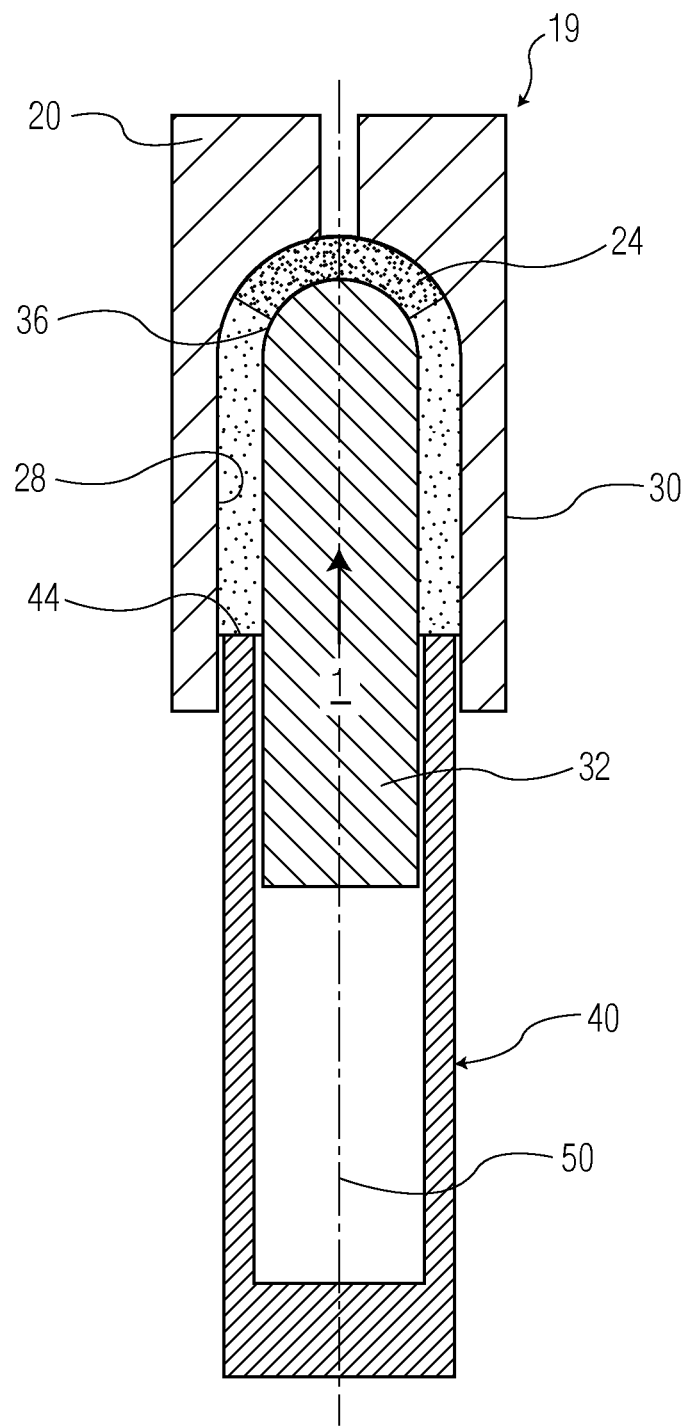
FIG. 3 is a cross-sectional view of the three mold parts in an intermediate position with proper compression at the pole.
Figure 4:
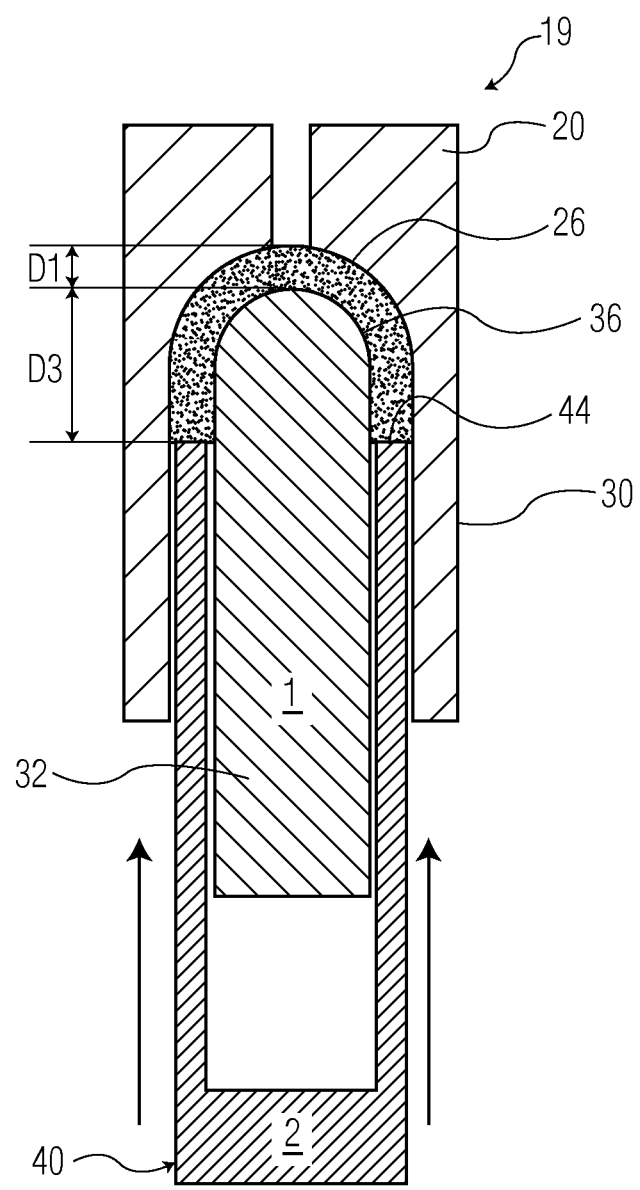
FIG. 4 shows the two moveable rams of the three-part mold in its final position where the outer ram with an annular impact surface has now compacted the powder in the equatorial region.

FIGS. 2-4 show, schematically a three part mold 19 and how the three-part mold 19 is used to form the acetabular shell 10 of FIG. 1. Note that the three mold parts of FIGS. 2-4 are shown generally in cross-section and are in fact surfaces of revolution so that a hemispherical cup may be produced during the molding process. Referring to FIG. 2, there is shown a first mold part 20 having an entrance 22 for receiving the titanium powder 24. The first mold part 20 includes an inner part-spherical surface 26 and a cylindrical surface 28 housing the second and third mold parts. The outer surface 30 can be of any shape.

The three-part mold 19 includes a second mold part 32 having a cylindrical surface portion 34 and a part-spherical outer surface portion 36. Surface 36 forms the inner hemispherical surface of the acetabular shell typically used to receive the polyethylene bearing surface of the implant. It should be noted that the construct produced by the molding operation of the present invention will require further machining to provide the various locking mechanisms necessary for capture of the polyethylene bearing insert. In the preferred embodiment, second mold part 32 is in the form of a ram which may be moved vertically within the cylindrical walls 28 of first mold part 20. The third mold part, in the preferred embodiment, is a hollow cylinder denoted as 40 having a cavity 42 in which the cylindrical portion 34 of second mold part 32 is movably housed. Third mold part 40 includes an annular planar impact surface. Thus, third mold part 40 is cylindrical with a concentric outer wall 46 and inner wall 48 which produce the annular impact or ram surface 44.

FIG. 3 shows an intermediate position for the molding operation or process in which the second mold part 32 acts as a ram compacting the powder in the polar area of the hemispherical inner surface 26 of first mold part 20. Preferably this occurs prior to any movement of the third mold part 40. Note that the hydraulic parts which move the mold parts are not shown but are well known in the compression molding art. Immediately after surface 36 of part 32 compacts the powder 24 third mold part with its annular impact surface 44 is moved within surface 28 of first mold 20 and compacts the partially compacted powder and forming the acetabular shell 10 in the equatorial areas. It can be seen that the part-spherical surface 36 of second mold part 32 is initially spaced a distance D from the polar area of the spherical surface 26 of first mold part 20. Likewise the impact surface 44 of third mold part 40 is initially spaced a distance D2 from the spherical surface 36 and a distance of D2 plus D from the pole (at the base of bore 22) of inner surface 26 of first mold part 20. Bore 22 is closed at this point.

Referring to FIG. 4 it can be seen that after the movement of second mold part 32 and third mold part 40 to their final compression position the surface 44 is located a distance of D3 plus D1 from surface 26 of first mold part 20. It can be seen that the distance of travel of surface 44, to the distance of D2 plus D3 is approximately three times the travel of surface 36 which initially at distance D from surface 26 to distance D1. This is because as can be seen in FIGS. 2 and 3, the necessary compaction of the thicker wall in the axial direction along axis 50 of surface 44 is three times longer than the necessary travel of surface 36 for the approximately 50% compaction of the Ti powder. In the preferred embodiment, the first, second and third mold parts 20, 32 and 40 are all coaxially aligned along axis 50. The impact force produced by the powder contact surfaces of mold parts 32 and 40 is between 30 and 50 tons per square inch.

It is also possible to keep mold part 32 stationary and move part 20 into contact with the powder and then move mold part 40 into contact with the partially compacted powder. Also note that rams 32 and 40 need to be from opposite ends of the press to make the hemispherical shell or femoral component.

The motions and geometry of the mold schematic in FIGS. 2-4 are for example purposes only. Depending on the specific geometry of the part to be molded it may be advantageous to move the peripheral ram prior to the central ram. In addition, rams 32, 40 can move simultaneously but at different speeds so that each provides the necessary amount of compaction in the same amount of time (since the distances traveled are different).

It is also important to note that the motions in the mold are relative motions. Therefore, mold part 20 in FIGS. 2-4 that is illustrated as being fixed can in fact be a movable mold component while another part of the mold (such as 32 or 40) is fixed. Alternatively, two parts of a mold can be moving towards each other simultaneously.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for manufacturing a titanium acetabular cup shell comprising:
   obtaining a titanium sponge powder;
   providing a three part mold having a first part with a part-spherical inner surface, a second part comprising a first ram with a part-spherical outer impact surface and a third part comprising a second ram with an annular impact surface, the second and third parts aligned along an axis within the first part and the second part aligned along the axis within the third part and surrounded by the annular impact surface thereof;
   filling the first part with the titanium sponge powder;
   moving the second mold part-spherical outer surface and the third part annular surface towards the part-spherical inner surface of the first part into contact with the powder; and
   compacting the powder with the second part part-spherical outer impact surface and the third part annular impact surface.

2. The method as set forth in claim 1 wherein the second and third mold parts contact the powder simultaneously.

3. The method as set forth in claim 2 wherein the third mold part moves at a greater velocity relative to the first mold part than the second mold part.

4. The method as set forth in claim 1 wherein the second mold part contacts the powder prior to the third mold part contacting the powder.

5. The method of claim 4 wherein the second mold part remains in contact with the powder until after the third mold part contacts the powder.

6. The method as set forth in claim 1 wherein the powder is compacted to about 50% of its original volume by the mold parts.

7. The method as set forth in claim 6 wherein the third mold part moves three times as far relative to the first mold part after initially contacting the powder compared to the second mold part.

8. The method as set forth in claim 1 wherein a central axis of the annular impact surface is coaxial with an axis through a center and a pole of the first and second mold part part-spherical surfaces.

9. The method as set forth in claim 8 wherein the mold parts move with respect to each other in a direction parallel to the axis.

10. The method as set forth in claim 8 wherein the cylindrical impact surface of the third mold moves three times further with respect to the first part compared to the movement of the second part with respect to the first part.

11. The method as set forth in claim 1 wherein the second and third mold parts impact surface produce a pressure of 30 to 50 tons per square inch.

12. A method for manufacturing a titanium acetabular cup outer shell comprising:
   providing titanium sponge powder having an average size less than 20 mesh;
   providing a mold having three parts aligned along an axis, the mold having a first part comprising a part-spherical inner surface, a second part comprising a part-spherical outer impact surface and a third part having an annular impact surface, the second part and third part moveable with respect to the first part part-spherical inner surface;
   the axis forming a central axis of the first and second part spherical surfaces and the third part impact surface, the third mold part annular impact surface formed by concentric inner and outer cylindrical surfaces, the diameter of the inner cylindrical surface of the third part greater than a maximum diameter of the part-spherical outer surface of the second part and the outer cylindrical surface diameter of the third mold part being less than a maximum diameter of the part-spherical inner surface of the first mold part wherein the second mold part is slidably nested within the third mold part and the third part is nested in the first mold part; and filling the first mold part with powder and compacting the powder with the second and third parts to form a part-spherical shell.

13. The method as set forth in claim 12 wherein the second and third mold parts contact the powder simultaneously.

14. The method as set forth in claim 13 wherein the third mold part moves at a greater velocity relative to the first mold part than the second mold part.

15. The method as set forth in claim 12 wherein the second mold part contacts the powder prior to the third mold part contacting the powder.

16. The method of claim 15 wherein the second mold part remains in contact with the powder until after the third mold part contacts the powder.

17. The method as set forth in claim 12 wherein the powder is compacted to about 50% of its original volume by the mold parts.

18. The method as set forth in claim 17 wherein the third mold part moves three times as far relative to the first mold part after initially contacting the powder compared to the second mold part.

19. The method as set forth in claim 12 wherein a central axis of the annular impact surface is coaxial with an axis through a center and a pole of the first and second mold part part-spherical surfaces.

20. The method as set forth in claim 19 wherein the cylindrical impact surface of the third mold moves three times further with respect to the first part compared to the movement of the second part with respect to the first part.

21. The method as set forth in claim 12 wherein the second and third mold parts impact surface produce a pressure of 30 to 50 tons per square inch.

* * * * *